United States Patent
Ryan et al.

(10) Patent No.: US 6,403,377 B1
(45) Date of Patent: *Jun. 11, 2002

(54) HEMATOLOGY CONTROL AND SYSTEM FOR MULTI-PARAMETER HEMATOLOGY MEASUREMENTS

(75) Inventors: Wayne L. Ryan; John Scholl, both of Omaha, NE (US)

(73) Assignee: Streck Laboratories, Inc., La Vista, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/934,463

(22) Filed: Aug. 21, 2001

Related U.S. Application Data

(63) Continuation of application No. 09/740,509, filed on Dec. 19, 2000, which is a continuation of application No. 09/504,816, filed on Feb. 16, 2000, now Pat. No. 6,221,668, which is a continuation-in-part of application No. 09/378,608, filed on Aug. 20, 1999, now Pat. No. 6,200,500.

(51) Int. Cl.$^7$ .............................................. G01N 33/49
(52) U.S. Cl. .......................... 436/8; 252/408.1; 436/10; 436/15; 436/16; 436/807
(58) Field of Search ............................... 436/8, 10, 15, 436/16, 18, 807; 252/408.1

(56) References Cited

U.S. PATENT DOCUMENTS

| | | |
|---|---|---|
| 3,558,522 A | 1/1971 | Louderback et al. |
| 3,574,137 A | 4/1971 | Decasperis et al. |
| 3,607,783 A | 9/1971 | Tata |
| 3,640,896 A | 2/1972 | DeCasperis |
| 3,873,467 A | 3/1975 | Hunt |
| 4,099,917 A | 7/1978 | Kim |
| 4,160,644 A | 7/1979 | Ryan |
| 4,179,398 A | 12/1979 | Hunt |
| 4,198,206 A | 4/1980 | Ryan |
| 4,219,440 A | 8/1980 | Runck et al. |
| 4,264,470 A | 4/1981 | Chastain, Jr. et al. |
| 4,299,726 A | 11/1981 | Crews et al. |
| 4,324,686 A | 4/1982 | Mundschenk |
| 4,324,687 A | 4/1982 | Louderback et al. |
| 4,358,394 A | 11/1982 | Crews et al. |
| 4,389,490 A | 6/1983 | Crews et al. |
| 4,390,632 A | 6/1983 | Carter, II |
| 4,425,334 A | 1/1984 | Hunt |
| 4,436,821 A | 3/1984 | Ryan |
| 4,698,312 A | 10/1987 | Wong et al. |
| 4,704,364 A | 11/1987 | Carver et al. |
| 4,711,852 A | 12/1987 | Jacobson et al. |
| 4,745,071 A | 5/1988 | Lapicola et al. |
| 4,751,179 A | 6/1988 | Ledis |
| 4,777,139 A | 10/1988 | Wong et al. |
| 5,008,021 A | 4/1991 | Conner et al. |
| 5,008,201 A | 4/1991 | Ryan |
| 5,262,327 A | 11/1993 | Ryan |
| 5,270,208 A | 12/1993 | Ryan |
| 5,320,964 A | 6/1994 | Young et al. |
| 5,432,089 A | 7/1995 | Ryan et al. |
| 5,459,073 A | 10/1995 | Ryan |
| 5,460,797 A | 10/1995 | Ryan |
| 5,492,833 A | 2/1996 | Rodriguez et al. |
| 5,529,933 A | 6/1996 | Young et al. |
| 5,616,501 A | 4/1997 | Rodriguez et al. |
| 5,672,474 A | 9/1997 | Ryan |
| 5,677,145 A | 10/1997 | Ryan |
| 5,731,205 A | 3/1998 | Ryan |
| 5,736,402 A | 4/1998 | Francis et al. |
| 5,811,099 A | 9/1998 | Ryan |
| 5,858,789 A | 1/1999 | Francis et al. |
| 5,858,790 A | 1/1999 | Kim et al. |
| 5,888,790 A | 3/1999 | Cahoon et al. |
| 5,945,340 A | 8/1999 | Francis et al. |
| 5,981,282 A | 11/1999 | Ryan |

FOREIGN PATENT DOCUMENTS

| | | |
|---|---|---|
| WO | WO 93/17329 | 9/1993 |
| WO | WO 93/17330 | 9/1993 |

OTHER PUBLICATIONS

Greenfield, S. M. et al., "Inhibition of Red Cell Membrane Lipid Peroxidation by Sulphasalazine and 5–Aminosalicylic Acid," *Gut* 32:1156–1159 (1991). No Month.

Lombarts, A.J.P.F. et al., "A Stable Human Platelet–White Blood Cell Control for the Coulter Model S–Plus II," *Clinica. Chimica. Acta.* 130:95–102 (1982). No Month.

Lombarts, A.J.P.F. et al., "A White Blood Cell Control of Long–Term Stability," *Clinica. Chimica. Acta.* 129:79–83 (1983). No Month.

Negre–Salvayre, A. et al. "Protective Effect of a–Tocopherol, Ascorbic Acid and Rutin against Peroxidative Stress Induced by Oxidized Lipoproteins on Lymphoid Cell Lines," *Biochem. Pharmacol.* 42:450–453 (1991). No Month.

Sorette et al., "Improved Isolation of Normal Human Reticulocytes via Exploitation of Chloride–Dependent Potassium Transport," *Blood*, vol. 80, No. 1, (Jul. 1, 1992); pp. 249–254.

Application Serial No. 09/315,335, filed May 20, 1999, White Blood Cell Hematology Control.

Application Serial No. 09/390,953, filed Sep. 7, 1999, White Blood Cell Hematology Control.

Application Serial No. 09/015,567, filed Jan. 30, 1998, White Blood Cell Hematology Control.

*Primary Examiner*—Deborah Jones
*Assistant Examiner*—Jennifer McNeil
(74) *Attorney, Agent, or Firm*—Dobrusin & Thennisch PC

(57) ABSTRACT

Hematology control compositions and systems used to measure a plurality of parameters in a blood sample are provided. The hematology control compositions are particularly useful as a control for multi-parameter, automated instrument systems. The control compositions comprise a reticulocyte component, a white blood cell component, a red blood cell component, a nucleated red blood cell component, a platelet component and a reticulated platelet component. Methods of making and using the control compositions are also provided.

53 Claims, No Drawings

US 6,403,377 B1

HEMATOLOGY CONTROL AND SYSTEM FOR MULTI-PARAMETER HEMATOLOGY MEASUREMENTS

CLAIM OF BENEFIT OF EARLIER FILING DATE

This application is a continuation of copending application Ser. No. 09/740,509 filed on Dec. 19, 2000, which is a continuation of application Ser. No. 09/504,816 filed on Feb. 16, 2000, now U.S. Pat. No. 6,221,668 which is a continuation-in-part of application Ser. No. 09/378,608 filed on Aug. 20, 1999, which issued Mar. 13, 2001 as U.S. Pat. No. 6,200,500. Applicants hereby claim the benefit of the filing date of such applications for all purposes and to the extent permitted in accordance with 35 U.S.C. Section 120.

FIELD OF THE INVENTION

The present invention relates generally to hematology control compositions and systems and, more particularly, to a hematology control composition and system used to measure a plurality of parameters in a sample of blood with a multi-parameter automated hematology instrument.

BACKGROUND OF THE INVENTION

Hematology controls for various automated instruments that measure, for example, red and white blood cell counts and platelet counts, are known in the art and are described in the following U.S. Pat. Nos. 3,558,522; 3,873,467; 4,179,398; 4,219,440; 4,299,726; 4,324,687; 4,358,394; and 4,436,821 (incorporated by reference herein). Currently, blood analysis requires the use of one or more of several different instruments and, subsequently, different blood samples and blood sample preparations to analyze the various components of blood. Several hematology instruments, however, now have the capability of measuring various parameters of blood without requiring separate sample preparation for each parameter being tested. Such instruments include the Beckman Coulter STKS or Gen-S Systems, the Abbott Cell-Dyn 4000 Hematology System, Bayer ADVIA 120, and the Sysmex XE2100 System. These improved automated instruments can measure one or more of: 1) reticulocytes, 2) red blood cells, 3) nucleated red blood cells, 4) platelets, 5) reticulated platelets, 6) white blood cells, including lymphocytes, monocytes, neutrophils, eosinophils, basophils, and 7) white blood cells with all phenotypes. It would thus be desirable to provide a hematology control composition that could be used as a control in connection with these instruments.

In the preferred embodiment, a hematology control composition for use with a multi-parameter automated hematology instrument includes a liquid suspension of particulates that has measureable characteristics like whole blood. The control composition includes one or more blood cells (i.e. cells handled or treated to simulate such a component as found in whole blood) or their analogs (collectively referred to as blood cell components), that may or may not be fixed, stabilized, or prepared by other treatment prior to final suspension. In different embodiments, the blood cell components may be derived from a source that will exhibit the size, shape or other measurable characteristics of human, animal, or other whole blood. By way of examples, U.S. Pat. Nos. 4,198,206; 4,436,821; 5,008,021; 5,262,327; 5,270,208; 5,432,089; 5,460,797; 5,672,474; 5,677,145; 5,731,205; 5,811,099 and 5,981,282, which are each hereby incorporated by reference, each contain examples of these types of blood cell components. The control has one or more blood component to resemble corresponding components in whole blood when measured by the multi-parameter automated hematology instrument. When so measured, the control composition would assist in the calibration, operation, and accumulation of quality assurance data for the multi-parameter automated hematology instrument.

Also of potential interest may be U.S. Pat. No. 5,888,790 and "Improved Isolation of Normal Human Reticulocytes via Exploitation of Chloride-Dependent Potassium Transport," Sorette et al., Blood, Vol. 80, No. 1 (Jul. 1), 1992: pp. 249–254; hereby incorporated by reference.

SUMMARY OF THE INVENTION

A hematology control and system for multi-parameter hematology measurement is provided. The hematology control provides values for the various constituents of blood that the multi-parameter hematology instrument is capable of measuring. The hematology control composition comprises components for simulating reticulocyte, white blood cell, red blood cell, nucleated red blood cell, platelet or reticulated platelet constituents of whole blood.

Methods of making and using the hematology control composition of the present invention are also provided herein.

The system of the present invention also includes a hematology instrument, a control, and may further include output or readout devices. In one embodiment the system includes other peripheral devices, such as a device for tracking samples and associating them with particular data, such as a bar-code scanner system.

DETAILED DESCRIPTION OF THE PREFERRED EMBODIMENTS

The hematology control composition of the present invention comprises components for simulating one or more of the following constituents of whole blood: reticulocytes, white blood cells, red blood cells, nucleated red blood cells, platelets, or reticulated platelets. In one embodiment the components are suspended in an isotonic medium, preferably including lipoprotein. The hematology control composition of the present invention provides values for various constituents of blood that a hematology instrument, such as a multi-parameter hematology instrument, is capable of measuring. Examples of multi-parameter hematology instruments include those available commercially without limitation, under the designations Beckman Coulter STKS or Gen-S Systems, the Abbott Cell-Dyn 4000 Hematology System, Bayer ADVIA 120 System, the Sysmex XE2100 System, or the like.

The present discussion includes multiple approaches to making a control in accordance with the present invention, it being recognized that one highly preferred embodiment contemplates a control having components that simulate the characteristics of whole blood for purposes of obtaining readouts on a Beckman Coulter GEN-S instrument for red blood cells, the five populations of white blood cells, reticulocytes and platelets. Thus, a suspension is provided that includes a plurality of particles that exhibit similar light scattering, conductivity, impedance, optical (including fluorescence), photometric, or other property responses detected by the instrument in operation, as would the corresponding components of whole blood.

It will be appreciated that the term "control composition" as used herein means one or more blood components (i.e., blood constituents as well as analogs thereof), which when combined or used alone, sufficiently simulate the relevant characteristics of whole blood for which the instrument tests. The following addresses the preparation of various of the constituent components. The control of the present invention contemplates an admixture of two or more blood components, and preferably a reticulocyte component and a component simulating at least three, and preferably five subpopulations of white blood cells. Percentages are by volume unless otherwise indicated.

Reticulocyte Component

The reticulocyte component of the control composition includes a component that exhibits the relevant characteristics for detection of reticulocytes using a hematology instrument in accordance with the present invention. Accordingly, the control may suitably contain stabilized reticulocytes (that is, immature anucleate red blood cells containing some ribonucleic acid) or an analog thereof. For example, among possible embodiments, the reticulocyte component may comprise true mammalian reticulocytes prepared for instance by mammalian (e.g. human) red blood cell encapsulation or by isolation from whole blood. The reticulocyte component is prepared in any suitable manner. See, eg., U.S. Pat. No. 5,432,089, incorporated by reference. Alternatively, it is possible to obtain suitable reticulocytes by obtaining blood from an anemic animal (e.g., a pig, goat, rabbit or the like).

In one particularly preferred embodiment, the reticulocyte component is prepared by an encapsulation method, using non-reticulocyte blood cells, such as red blood cells from a human or other source. The red blood cells are encapsulated and stabilized. By way of illustration, in one embodiment, red blood cells having a relatively high MCV (e.g., about 85 to about 95 EL, and more preferably about 88 to about 92 fL) are provided.

The cells are washed in a suitable diluent (e.g., about 0.15 M NaCl) in one or more washing steps. The cells are then concentrated to a desired hematocrit value, e.g., greater than about 50%, and more preferably greater than about 70%.

The cells are then encapsulated with RNA. By way of example, RNA is encapsulated into the red blood cells by a suitable lysis step, e.g., by hypotonic lysis. This may be done in a number of ways, including by mixing red blood cells with a solution of RNA having an appropriate pH and osmolarity. For instance the solution may contain a minor amount of RNA (more preferably about 1%), and has a pH between about 7 and 8 (more preferably about 7.6). The solution is adjusted (e.g. with NaCl) to obtain an osmolarity of about 40 mOsm.

The red blood cells are mixed with the RNA solution in a suitable proportion, which may vary as desired. In a present preferred embodiment, the volume ratio of packed red blood cells to RNA solution is about 0.8 to about 1.2:about 1 to about 2, and more preferably is about 1:1.4. Before lysing, or at an early stage of the lysing, the red blood cells and the RNA solution are pre-incubated, such as by heating to above room temperature (e.g., about 37 degrees C.). The cells are lysed in the admixture, and thereafter, the red blood cells are re-sealed. By way of example, the red blood cells are re-sealed by introducing them to a salt solution and then heating above room temperature (e.g., adding about 0.15 volume of about 12% NaCl solution, and then heating or annealing the cells to about 37 degrees C. for about one hour).

The resulting mixture is poured into a separatory funnel and allowed to incubate for a suitable time, e.g., for at least about 18 hours at room temperature. Thereafter, cells from the bottom portion of the funnel are collected (e.g., from about the bottom 70% or lower). The cells are washed with a suitable diluent, such as the diluent from Table 1 or 4. Optionally, about 0.5 to about 5.0% and more preferably about 0.75% of Streck Laboratories product number 233301, also known as STA-CELL (available from Streck Laboratories (Omaha, Nebraska)) is added. In the present illustrated embodiment, the cells are thus treated in a manner that would make them susceptible to a detection stain (e.g., methylene blue).

In another embodiment, the reticulocyte component is fixed (such as with an aldehyde or other suitable fixative) in a lactose or other suitable diluent. A like diluent absent the fixative may also be employed for washing.

White Blood Cell Component

In the present embodiment, the component of the control that is to simulate the characteristics of white blood cells in whole blood is prepared from a biological material. More specifically, the material is a cellular biological material, and preferably the material includes human white blood cells (although blood cells from any suitable animal may be employed). In a preferred embodiment of the present invention, the white blood cell component includes materials for replicating the relevant measurable characteristics for some or all of each of the five white blood cell types, namely, lymphocytes, monocytes, neutrophils, eosinophils and basophils, and they in turn are provided at their art-disclosed levels (see, e.g., Table 6).

The white blood cell component of the hematology control composition comprises a blood cell (e.g. white blood cell) or analog thereof, selected from the group consisting of white blood cells for various cellular types, white blood cells for all phenotypes, and mixtures thereof U.S. Pat. Nos. 5,270,208 and 5,262,327, incorporated herein by reference, provide examples of a suitable white blood cell component (see also U.S. Pat. No. 5,529,933, hereby incorporated by reference). Of course, the skilled artisan will appreciate that the subject invention is not limited to white blood cell components prepared from only white blood cells. Analogs prepared from any of a variety of other souces are possible, including but not limited to red blood cells from birds, reptiles, mammals, etc.

The cells are provided in packs (e.g., 2 to 3 packs per bottle). The cells are treated by a series of steps for selectively lysing any undesired blood cells present in the material as provided; for washing the cells; and for fixing or otherwise stabilizing the cells.

Selective lysing may be accomplished in any suitable manner, for instance, by contacting the undesired blood cells with a lysing agent. Any suitable lysing agent may be employed. Buffered halides, such as ammonium chloride and Trizma Based (e.g., about 7.5 g ammonium chloride and 2 g Tris per liter), illustrates one suitable class of lysing agents, where the undesired cells include red blood cells. Lysing is accomplished through a series of consecutive washing steps with the lysing agent. Optionally, before the lysing, the cells are subjected to a preliminary fixing step, such as by contacting them with a suitable fixing agent, heating them or both. For instance, the cells are contacted with a buffered antimicrobial saline solution (optionally including a diluent as described in Table 4) including a suitable amount of a fixative (e.g., about 0.11% formaldehyde).

The lysing may be done in a single step or a plurality of steps (e.g., for about one hour, then for about 25 minutes), where after each step, the lysing agent is removed and fresh agent is introduced. After lysing, the cells are washed to remove the lysing agent. Any suitable wash composition and technique may be employed. For instance, the aforenoted buffered antimicrobial saline solution (absent a fixing agent) may be employed. Using this solution the cells are washed in at least one step and preferably two steps, wherein the cells are centrifuged at a suitable rate (e.g. about 900 rpm for about 10 minutes) (e.g., about 200 xg).

Prior to fixing, it may be preferable to further pre-treat the cells in an albumin-containing diluent, such as about 2% BSA in a diluent such as that of Table 1. Preferably the diluent has a pH of about 8 and an osmolarity of about 175 to about 300 (e.g. about 215). Any suitable period of pre-treatment may be employed, e.g., about one hour, when maintained at about 6 degrees C.

The cells are fixed in any suitable manner sufficient to denature the protein on the cell surface. The cells may be heated, contacted with a fixing agent or both. The skilled artisan will recognize that, though the preferred fixing agent is an aldehyde, any suitable agent (preferably in a hypotonic solution) may be used, including for instance, those containing an aldehyde, an alcohol, a heterocyclic urea (e.g., diazolidinyl urea (known as DU), imidazolidinyl urea (known as IDU) or a mixture thereof) or a mixture thereof Among the suitable fixing agents, one particularly effective alcohol-containing agent is 50% by volume—[1-methyl-2-(5-methyl-3-oxazolidinyl)-ethoxy] methoxy] methanol (e.g., NUOSEPT 145, from HULS America, Inc.), or a mixture therof. In one present preferred embodiment, the aldehyde is selected from the group consisting of formaldehyde, glutaraldehyde, and mixtures thereof.

By way of illustration, a fixing admixture is prepared to include about 10 parts cells, about 20 parts distilled water, an agent for enhancing osmolarity across the cell membrane, for aiding in the formation of clusters in scattergram population readouts or both (e.g., about 5 g/l of a sugar, such as sorbitol), an agent for helping to stabilize the readout of monocytes (e.g., about 4% DU), and a fixing agent, such as about about 4 parts formaldehyde, and about 0.1 parts glutaraldehyde. Fixing is performed for a suitable amount of time and at a suitable temperature. Using this fixing agent, for example, fixing is performed for about 2 to about 3 days at about 22 degrees C. (i.e., warmed prior to fixing after refrigeration).

Fixed cells are washed with a suitable rinse material (e.g., a cell stabilizer in a diluent) to remove the fixing agent. By way of illustration, two washes are made during centrifugation at about 900 rpm for about 10 minutes (e.g., about 200 xg), in a solution including a metal halide (e.g., about 5% NaF) cell stabilizer in a diluent (e.g. a diluent having the composition as outlined in Table 2).

In another illustrative embodiment, when preparing the white blood cell component for the control composition of the present invention, the cells are obtained by standard separation from whole blood or from portion of previously fractionated whole blood containing the desired cell population. The cells are resuspended, for instance, in a phosphate buffered solution containing polyethylene glycol 20,000 (PEG), ethylenediamine tetraacetic acid (EDTA) and magnesium gluconate with 2% bovine serum albumin. The osmolarity of this solution is preferably sufficient to swell the white blood cells prior to fixation (e.g. about 215 mosm). The cells may then be stored in this solution, e.g. at about 6° C. for 1 hour.

The cells are fixed in a suitable media in order preferably to denature the surface or otherwise accomplish preserving the cell morphology. To illustrate, in one embodiment, in a solution of distilled water containing 5 g/l sorbitol, 7.4% formaldehyde and 0.125% glutaraldehyde. Of course, other suitable fixing agents may be used in suitable amounts. In a highly preferred embodiment, the white blood cells and the fix solution are maintained at a temperature sufficient to provide a proper white blood cell position (e.g. between about 4° C. and 12° C.). The fixative is added to the cells at a suitable ratio. For example, in one embodiment, a ratio of between 10 ml of cell suspension to 24 ml of fix solution is used. The distilled water in the fix solution swells the white blood cells further, while the fixative stabilizes the cell membrane. The cells are thus left in the fixative for 2 days at room temperature.

After fixation, the cells preferably are washed. In one aspect, they are washed in a phosphate buffered solution. One such solution contains polyethylene glycol, (PEG), ethylenediaminetetraactic acid (EDTA), magnesium gluconate and bovine serum albumin. Lipoprotein concentrate is added at 150 mg/dl HDL to store the cells prior to use in order to improve the stability of the scattergram position while the white blood cells are waiting to be added to the other components of the control composition.

It will be appreciated that white blood cells prepared as described in U.S. Pat. No. 5,459,073 (incorporated herein by reference) for flow cytometry may be employed for phenotyping. By mixing the two types of white cells, both requirements can be met, i.e., white blood cells for various cellular types and phenotypes, as the cells prepared for phenotyping generally should not interfere with the position of other white blood cells on the histograms/scattergrams.

In controls for certain instruments, white blood cells may need to be diluted or concentrated, for example, for the Cell-Dyn instruments a dilution to a count of 10,000 is preferred.

Red Blood Cell Component

In the present embodiment, the component of the control that is to simulate the characteristics of red blood cells in whole blood is prepared from a bio-compatible material. More specifically, the material is a cellular biological material, and preferably the material includes human red blood cells (although analog blood cells from any suitable animal may be employed).

The cells as provided are separated from the liquid medium or supernatant in which it is supplied through any suitable separation technique, including but not limited to centrifugation, filtration, or the like. The cells are washed in a series of one or more (e.g., 3) consecutive washing steps, pursuant to which excess supernatant is removed. The cells preferably are washed in a (e.g. such as the diluent of Table 2) and optionally one or more additional components selected from the group consisting of a cell stabilizer, an albumin, an agent for reducing the likelihood of cell hemolysis in the presence of oxygen, and mixtures thereof. In a more preferred aspect, the additional components are selected from the group consisting of a metal halide cell stabilizer, bovine serum albumen (BSA), an antioxidant and mixtures thereof. In still a more preferred embodiment, the diluent is one such as that of Table 4, and it will include about 0.003 to about 0.010 (and more preferably about 0.005%) NaF, about 2% BSA, about 0.005 to about 0.020 (and more preferably about 0.010%) sulfasalizine. The diluent of Table 1 likewise may be used as desired.

Optionally, depending upon the end use and commercial considerations, one or more agents for reducing the rate of degradation is employed in a suitable amount; for example, about 0.25 to about 2.0%, and more preferably about 0.75% of a material available from Streck Laboratories (Omaha, Nebraska) under the product number 233301 or the designation STA CELL (which material may also be suitably added for one or more of the other components). Further, optionally, the cells preferably are prepared in an environment substantially free of glucose. In yet another optional embodiment, the cells are fixed (e.g., by a suitable protein denaturation step, such as by glutaraldehyde fixing) after washing and then further washed.

The cells may be washed for any suitable period of time, and resuspended (in the same wash or a different one, e.g., one having a higher concentration) any suitable number of times.

The skilled artisan will appreciate that the red blood cells may be washed free of all other cellular material, such as by using a magnesium gluconate diluent.

By way of further illustration, in another embodiment, concentrated red blood cells are provided, separated from associated supernatant, and concentrated human red blood cell packs are suspended in a solution (e.g. phosphate buffered solution containing PEG (MW=20,000)) and allowed to settle overnight. The supernatant is then removed and 0.5% NaCl with PEG is added in an equal volume to the packed red blood cells and allowed to set at room temperature for 45 hours. The supernatant is again removed and the cells are resuspended in the NaCl solution and stored at 6° C. overnight. The packs are further checked for excessive hemolysis and removed from the inventory. The remaining packs are pooled into batches based on the MCV's, wherein twelve to fourteen packs are combined to make a batch. The batches are again resuspended in the NaCl solution for about 4–5 hours at room temperature. Of course, other times and temperatures may be employed.

Each batch is resuspended into a phosphate buffered solution containing PEG, EDTA and magnesium gluconate. The cells are allowed to settle, the supernatant is removed and the cells are resuspended in the above solution with lower PEG concentrations for storage up to 90 days at 6° C.

One diluent efficient in stabilizing the red blood cells on the Coulter STKS includes a phosphate buffered solution containing PEG, $Na_2EDTA$, magnesium gluconate and an antioxidant (e.g., sulfasalazine or $\alpha$-tocopherol), wherein the antioxidant is added to prevent hemolysis when the lipoprotein is added to the control composition of the present invention. The final diluent also contains about 2% bovine serum albumin to improve the position of the white blood cells. After the cells have been washed into this diluent, STA-CELL from Streck Laboratories (Omaha, Nebraska) is added at 0.75% to the total volume of red blood cells to give added stability to the MCV'S.

Optionally, in certain applications, it may be desirable to fix the red blood cells, after removing excess red blood cells, such as by a slow centrifugation. By way of example, for such an embodiment, the diluent of Table 1 is employed. Cells are washed and resuspended in the diluent to a suitable concentration (e.g. about $4 \times 10^6/mm^3$). Preferably the pH is about 7 and there is no glucose in the suspension. Approximately one to one proportions of the cells are admixed with the diluent and a suitable amount of a fixative (e.g., about 0.007% to about 0.01% glutaraldehyde (by count)) for a suitable period and at a suitable temperature (e.g., 22 degrees C. for about one or two days). The resulting cells are then washed a plurality of times (e.g., about 3 to about 8) in a like diluent (preferably at a pH of between 7 and 8). The cells are centrifuged at about 1500 for about 15 minutes. Decanting and sonication is performed as needed. Moreover, the cells may be further treated as desired by the addition of a suitable amount of STA-CELL (e.g., about 0.75%) from Streck Laboratories, Inc. (Omaha, Nebr.).

Nucleated Red Blood Cell Component

When employed, the nucleated red blood cell component of the control composition of the present invention comprises nucleated red blood cells or an analog thereof, such as avian red blood cells, e.g., turkey or chicken red blood cells. For example, turkey red blood cells are washed into a phosphate buffered solution and set to a count of about $1 \times 10^5/mm3$. The cells are fixed with a phosphate solution (volume equal to the cell volume)+0.4% v/v glutaraldehyde, at room temperature for one day and then washed into a phosphate buffer.

The fixed turkey red blood cells are added to the control composition of the present invention to yield a cell count equal to at least 10% of the white blood cell count in order to produce NRBC flags on the Coulter STKS or the Cell-Dyne 4000 manufactured by Abbott Laboratories. Though the present example contemplates the use of turkey cells, cells from other cell sources may be employed as the skilled artisan will appreciate.

Platelet Component

In a preferred embodiment of the present invention, the hematology control composition additionally provides a platelet component, preferably a simulated platelet component. Among other possible types, the platelet component may comprise stabilized human platelets or platelets simulated from goat, bovine or porcine blood cells. In one embodiment, they are prepared from red blood cells. See, U.S. Pat. Nos. 4,160,644 and 4,198,206, incorporated herein by reference, disclose an example of a suitable platelet reference control and methods of preparation. The skilled artisan will appreciate a number of other techniques for preparing simulated platelets.

In general, how the platelets are prepared may depend upon the source of the cells (i.e., whether they are animal blood cells to be shrunken, swollen or otherwise sized or shaped to resemble platelets, or whether they are platelets from blood). In general, the cells are washed, optionally pre-fixed, sized and shaped, and then fixed or otherwise stabilized in terms of size and shape, and neutralized.

By way of example, the platelet component is prepared from animal blood cells, such as goat red blood cells. The cells are washed one or more times (e.g., about three times) in a suitable buffered solution such as a buffered saline solution (e.g., phosphate buffered saline solution). The solution may also include a suitable amount of a chelating agent (e.g., about 1% ethylene diamine tetraacetic acid (EDTA)).

The cells optionally are prefixed in a suitable maimer to aid in the step of sizing and shaping them. By way of illustration, the cells are contacted with a suitable pre-fix solution ((e.g., one to one in the initial wash solution having a fixative (e.g., about 0.0085% of glutaraldehyde)). The amount of such fixing agent of course may be suitably adjusted as needed to control the sizing rate (e.g., the shrinkage rate). Preferably the pre-fix solution is warmed to an elevated temperature (e.g., about 30 degrees C.), and prefixing is performed for a sufficient time at such temperature (e.g., about 90 minutes). After the pre-fix step, the supernatant is removed, such as by centrifuging, aspirating or both.

In instances where the sizing and shaping is performed to shrink the cells and form a simulated platelet structure, the cells preferably are lysed in a suitable manner (e.g., using a lytic agent such as ammonium chloride tris). During lysing, the cell size and shape may be monitored using a suitable instrument such as the H3 by Bayer Corporation (a hematology analyzer with a laser optical detection system). The cells are then washed one or more times with a suitable diluent (e.g., the diluent of Table 3)

Like with the aforenoted blood cells, the simulated platelets are fixed in any suitable manner, preferably one that will denature the protein on the cell surface. In a particularly preferred embodiment, the cells are fixed in a one to one solution with a diluent such as that of Table 3 and about 0.1% formaldehyde. Preferably the temperature of the fixing solution is elevated (e.g. about 37 degrees C.) for a sutiable period of time (e.g., about 3 days).

The cells are then washed with a suitable wash to remove the fixative, preferably also taking measures to neutralize any unreacted fixative that has not bound to the cell surface. To illustrate, preferably where the fixative is an aldehyde, a suitable amount of a glycine solution is employed in the wash. One or more additional washing steps may be performed, using one or more additional washes, as desired. For instance, subsequent washing steps may be employed using the wash composition of Table 3, Table 4 or a mixture thereof It will be appreciated that the platelet component can be made from human blood, using any suitable process. By way of example, without limitation, human blood is provided (preferably in a diluent having a fixative (e.g., a diluent such as that of Table 4 with about 0.10% formaldehyde). Optionally, red blood cells are removed, and the resulting cells are admixed with fixed cells. For instance, the red cells are centrifuged in quantities of about 400 ml per container for about 10 minutes at about 900 rpm).

As-provided cells are placed in a fixative (e.g., about one to one proportions in a diluent such as that of Table 3 with a suitable amount of a fixative (e.g., about 0.075% glutaraldehyde)). Fixing is done at about 22 degrees C. for about 2 days. Following fixation, centrifugation is performed at about 1800 rpm for about 20 minutes (for 400 ml container). The two separate collections of cells are brought together and washed (such as in a 1× diluent like that of Table 1), and then centrifuged (e.g. at about 1800 rpm for about 20 minutes). Optionally, the platelets are decanted from residual red blood cells. Sonication may be used as desired to address platelet clumping. Decantation may also be used as desired to assure debris and red blood cells are removed.

Resulting materials are then resuspended in a diluent. An example of a suitable diluent would be that of Table 1 having no glucose and a pH of about 7.

Reticulated Platelet Component

In another embodiment of the present invention, the control composition comprises a reticulated platelet component. To illustrate, without limitation, goat red blood cells with encapsulated nucleic acids would constitute one example of a reticulated platelet component useful for the present invention. Other analogs may be used as well.

By way of further illustration, in another embodiment, reticulated platelets for the control composition of the present invention are prepared by inducing a porous blood cell membrane to permit entry of RNA into a cell, hemoglobin to leave, or both. The then cells are sized or shaped and stablizied. To illustrate, goat red blood cells are placed in a solution of about 0.9% NaCl and concentrated to 70–80% hematocrit (HCT). Equal volumes of concentrated red blood cells and 4% RNA solution (20 mls of each) adjusted to 300 mosm with a suitable salt (e.g., KCl) are mixed together and dialyzed against 500 mls of a hypotonic solution, such as one containing glycerol (osm=90–100), for 90 minutes at 6° C. Dialysis is required to slowly change the osmolarity without damaging the cells. The resulting osmolarity change in the red blood cell solution is from about 300 mosm to about 150 mosm. This process creates holes in the cell membrane to allow the RNA in the red blood cell solution to enter the red blood cells.

The osmolarity is brought back to isotonicity by dialyzing the red blood cells containing RNA against an isotonic solution. This dialysis is at room temperature for 30 minutes and the final osmolarity of the cells is about 260 mosm. This process reseals the holes that were created by the hypotonic dialysis, thus trapping the RNA inside the cells.

Eighty milliliters of the resealing diluent containing 0.1% Nuosept 101 is added to the encapsulated red blood cells and the mixture is heated at 37° C. for 3 hours. This heating step helps to lyse the weakened cells from the encapsulation process and anneals the membranes of the encapsulated red blood cells.

To illustrate, goat red blood cells are separated from other constituents of goat whole blood. For instance, cells are washed into PBS three times to remove the plasma and white cells. The concentration is adjusted to $8\times10^6$/mm3 and fixed with a volume of PBS equal to the cells that contain 0.2240–0.320% glutaraldehyde, providing the amount of protection needed to allow proper lysis during the shrinkage step. The cells are incubated at 30° C. for one hour and centrifuged at 1200 RPM for 15 minutes. The supernatant is removed and the cell volume is adjusted to one-fourth of fixed volume.

An ammonium chloride solution is added to the cells to equal the original volume of fixed cells. Without intending to be bound by theory, the ammonium chloride solution creates holes in the membrane to allow hemoglobin to exit to the cells, while the glutaraldehyde protects from total lysis. The cells are monitored for hemoglobin loss based on (MPV) decreases on a Bayer H-1. When the MPV is at 10fl on the Bayer H-1, the cells are diluted with a phosphate buffered solution and centrifuged at 1800 RPM for 20 minutes. The supernatant is removed and the cells are washed to remove the free hemoglobin and shrink the membrane around the hemoglobin to produce an MPV of approximately 10fl on impedance instruments, such as the S+IV, manufactured by Beckman Coulter.

When the MPV is at 10fl on the H1, the cells are diluted with a phosphate buffered solution and centrifuged at 1800 RPM for 20 minutes. The supernatant is removed and the cells are washed to remove the free hemoglobin and shrink the membrane around the hemoglobin to produce an MPV of approximately 10fl on impedance instruments, such as the S+IV, manufactured by Beckman Coulter.

In a more preferred embodiment, to prevent further loss of hemoglobin and shrinkage of the membrane, the cells are fixed more than once, for instance, with 0.04% glutaraldehyde in a volume of phosphate buffered solution equal to the cell volume at a count of $1\times10^6$/mm3. The cells are left at room temperature overnight and then washed. Though the present example contemplates the use of goat cells, cells from other cell sources may be employed (such as stabilized human platelets) as the skilled artisan will appreciate.

Suspension Medium

The present invention relates to a method of making a hematology control composition for use with multi-parameter systems, comprising the step of mixing one or more of a reticulocyte (retic) component, a white blood cell component, a red blood cell component, a nucleated red blood cell component, a platelet component, and a reticulated platelet component in an isotonic suspension medium.

The components of the control preferably are suspended in appropriate concentrations a suitable suspension medium that permits the control to be processed through the automated instrument. The suspension medium thus has a pH of about 6.5 to about 8.5 and is isotonic. By way of example, among the possible embodiments of the present invention, the isotonic suspension medium may comprise a buffer, antioxidant, protein or a mixture thereof, e.g., magnesium gluconate/ethylene diamine tetraacetic acid (EDTA)/phospate buffer with nucleated red blood cells; the same buffer with the additives HDL, sulfasalazine and alpha tocopherol; or the same buffer with 3% albumin.

Lipoprotein

While BSA in any diluent present improves the white blood cell position on the scattergram, lipoprotein is also preferably used in an amount effective to provide a scattergram that represents whole blood, including the proper positioning of the five subpopulations of white blood cells. See U.S. Pat. Nos. 5,270,208 and 5,262,327 incorporated by reference. A lipoprotein source, preferably one consisting essentially of high-density lipoprotein (i.e., HDL) is added at about 0.5 to about 8.0% by volume of the control, and more preferably at about 100–175 mg/dl to the control composition and a-Tocopherol is further added to the lipoprotein source to reduce peroxides produced by the oxidation of the lipoproteins. An example of a suitable commercially available form of lipoprotein is SUPERTRATE (available from Bayer).

Admixing Components

Stock volumes of the constituent components are prepared in the following approximate concentrations:

RBC: $6.0 \times 10^6/mm^3$

WBC: $150,000/mm^3$

Platelets: $10 \times 10^6/mm3$

Retics: 50% of $5.5 \times 10/mm^3$ red count

NRBC: $0.5 \times 10^6/mm^3$

To prepare the final control composition, for example, in a 5 liter volume, stock volumes of the constituent components are combined as follows:

|  | Approximate Target Count | Approximate Volume Stock |
|---|---|---|
| RBC: | $4.5 \times 10^6/mm^3$ | 3,750 ml |
| WBC: | $8.0 \times 10^3/mm^3$ | 266 ml |
| Plt (platelets) | $225 \times 10^3/mm^3$ | 112 ml |
| Retic (%) | 3% | 370 ml |
| NRBC | 0.01% | 4.5 ml |

The combined constituents are brought to a final total volume of 5 liters by adding a suitable final diluent (e.g., prepared according to U.S. Pat. No. 5,262,327, incorporated herein by reference (preferably including SUPERTRATE or a like substance)). The skilled artisan will appreciate that there are other means and procedures to prepare this and other embodiments of the present invention. Moreover, concentrations can be varied to provide controls having predetermined abnormal readings when tested.

Using Control

The following discusses examples of methods of using the control composition to determine the accuracy and reproducibility of the operation of a multi-parameter automated hematology instrument. By way of example, a multi-parameter automated hematology instrument, such as a Beckman Coulter STKS or Gen-S Systems, the Abbott Cell-Dyn 4000 Hematology System, Bayer ADVIA 120, and the Sysmex XE2100 System, is provided, optionally with a slide preparation module. The claimed control composition is obtained or prepared which includes, by way of example, a treated stabilized human red blood cell component and a reticulocyte component with quality control values in an appropriate range, for example, 1.0%, 2.5%, and 9.0%, respectively. It is refrigerated prior to use. At the beginning of testing, the control composition is allowed to warm to room temperature for about fifteen minutes, mixed manually, and checked for resuspension of contents.

The control composition is prepared and analyzed by the same standard method as test samples which may be tested in batch quantities by the use of a suitable cassette having apertures for receiving test vials. After preparation, the control composition and test samples are analyzed by counting the population number of each subject component type with a multi-parameter automated hematology instrument, which will yield a visual display of the data.

For a Coulter System, the automated test instrument may employ technology known generally as VCS Technology (as marketed by Beckman Coulter). VCS generally analyzes cell samples in view of simultaneous volume conductivity and Scatter measurements. Ordinarily, a starting sample is employed in combination with suitable reagents (which may comprise a component of a kit) and physical agitation for lysing and cell measuring by way of flow cytometry.

Accordingly, the sample may be tested by the Coulter Principle of (DC) Impedance to measure the cell volume in an isotonic suspension.

Conductivity may be employed, for instance, by applying alternating current in the radio frequency range. Energy can penetrate the cell by short circuiting the cell membrane's bipolar lipid layer.

Information about the cells is also possible with light scatter techniques, such as from the scatter characteristics detected from cells in response to a coherent light source, e.g. a laser beam.

Of course, by no means is the mode of sample testing limited to the above. As mentioned other principles may be used.

The respective population counts obtained from the analysis are compared either to known reference value for each component type in the control composition, or by comparison of the population counts for each component types in the test sample with the corresponding values of components in the control composition. Data relating to the measurement of components in control composition and test samples is collected, monitored, stored, compared and analyzed by electronic means, such as a computer programmed with appropriate software and containing appropriate data file structure.

TABLE 1

| Reagents | Most Preferred Concentration |
|---|---|
| Distilled Water | 0.9 liter |
| Methyl Paraben | 0.40 g/l |
| PEG 20,000 | 3.00 g/l |
| EDTA, Disodium Salt | 7.04 g/l |
| Magnesium Gluconate | 3.92 g/l |
| Sodium Phosphate Dibasic Anhydrous | 2.68 g/l |
| Glucose | 6.0 g/l |
| Sodium Hydroxide pellets | 0.8 g/l |
| Adenosine | 0.25 g/l |
| Inosine | 0.25 g/l |
| Neomycin Sulfate | 0.40 g/l |
| Chloramphenicol | 0.15 g/l |

*q.s. to 1 Liter

Concentrated bovine serum albumin is added to the product at the time of combining the various cell types to make the protein concentration 3% of the liquid portion of the product.

TABLE 2

| Reagents | Most Preferred Concentration |
|---|---|
| Distilled Water | 0.9 liter |
| Methyl Paraben | 0.4 g/l |
| PEG 20,000 | 3.00 g/l |
| EDTA, Disodium Salt | 11.73 g/l |
| Magnesium Gluconate | 6.53 g/l |
| Sodium Phosphate Dibasic Anhydrous | 4.47 g/l |
| Glucose | 10 g/l |
| Sodium Hydroxide pellets | 1.40 g/l |
| Adenosine | 0.25 g/l |
| Inosine | 0.25 g/l |
| Neomycin Sulfate | 0.40 g/l |
| Sodium Fluoride | 0.05 g/l |
| Chloramphenicol | 0.15 g/l |

*q.s. to 1 Liter

TABLE 3

| Reagents | Most Preferred Concentration |
|---|---|
| Distilled Water | 0.9 liter |
| Methyl Paraben | 0.4 g/l |
| PEG 20,000 | 3.00 g/l |
| EDTA, Disodium Salt | 16.75 g/l |
| Magnesium Gluconate | 9.33 g/l |
| Sodium Phosphate Dibasic Anhydrous | 6.39 g/l |
| Sodium Hydroxide Pellets | 2.04 g/l |
| Adenosine | 0.25 g/l |
| Inosine | 0.25 g/l |
| Neomycin Sulfate | 0.40 g/l |
| Chloramphenicol | 0.15 g/l |

*q.s. to 1 Liter

TABLE 4

| Reagents | Most Preferred Concentration |
|---|---|
| Distilled Water | 1 liter |
| Methyl Paraben | 0.40 g/l |
| PEG 20,000 | 3.00 g/l |
| EDTA, Disodium Salt | 11.73 g/l |
| Magnesium Gluconate | 6.53 g/l |
| Sodium Phosphate Dibasic Anhydrous | 4.47 g/l |
| Glucose | 10 g/l |
| Sodium Hydroxide pellets | 1.40 g/l |
| Adenosine | 0.25 g/l |
| Inosine | 0.25 g/l |
| Neomycin Sulfate | 0.40 g/l |
| Sodium Fluoride | 0.05 g/l |
| Bovine Serum Albumin | 20 g/l |
| Sulfasalazine | 0.10 g/l |
| Chloramphenicol | 0.15 g/l |

*Cholestrol Supertrate containing α-Tocopherol is added to the product at the time of combining the various cell types. The cholestrol supertrate is added (2–3%) to make the α-Tocopherol concentration about 5 mg % in the product.

The skilled artisan will appreciate that a number of the ingredients have been disclosed by way of specific example, but that any of a number of alternative ingredients at the suggested or different concentration, may be suitably substituted for such ingredients. The following Table 5 illustrates examples of various alternatives, and also includes a brief discussion of the commonly employed concentration ranges when employed in the diluents of Tables 1–4. Though the ingredients are described by reference to a particular function, it should be appreciated that such discussion is presented without intending to be bound by theory. In some instances, the ingredient will perform a different or an additional function. Moreover, the skilled artisan will appreciate that reference in Table 5 to the functions, in the context of the present preferred embodiments, could be made to select additional alternatives. Thus, there is no intention to be bound to the breadth of any specific illustrative ingredient or concentration, where it is apparent that others may be advantageously be employed in addition to or as a substitute for such ingredient.

Likewise, as desired, ingredients may be deleted from the diluent. Thus, a combination of some of the ingredients may be suitably employed to achieve desired results.

Preferably, the diluent includes one or more agents that function as a surfactant, hemolysis inhibitor, red blood cell settler, MCV stabilizer, buffer, metabolite, osmolarity adjuster, antimicrobial, antifungal, protein source, positioner of white blood cell subpopulation, antioxidant, debris reducer or a mixture thereof.

TABLE 5

| Component | Preferred Concentration | Range of concentration | Others |
|---|---|---|---|
| Polyethylene Glycol (PEG MW 20,000) | 3.00 g/l | 1.00–10.00 g/l | PEG 8000, F68 |
| Disodium EDTA | 11.75 g/l | 7.00–17.00 g/l | Tetrasodium EDTA |
| Magnesium Gluconate | 6.50 g/l | 3.5–9.5 g/l | Lactose |
| Sodium Phosphate | 4.50 g/l | 2.5–6.5 g/l | Citrate, Borate, Trizma Base Sodium Bicarbonate |
| Glucose | 10.00 g/l | 0–10 g/l | Other sugars |

TABLE 5-continued

| Component | Preferred Concentration | Range of concentration | Others |
|---|---|---|---|
| Adenosine | 0.25 g/l | 0.1–1.0 g/l | Inosine |
| Neomycin sulfate | 0.40 g/l | 0.1–0.8 g/l | strepto-, kana-mycin |
| Chloramphenicol | 0.15 g/l | 0.1–0.4 g/l | Piperacillin |
| Methyl Paraben | 0.40 g/l | 0.20–1.20 g/l | Other antifungals |
| Bovine Serum Albumin | 30.0 g/l | 0.0–60.0 g/l | Other protein sources |
| Cholesterol Supertrate | 30 ml/l | 20–50 ml/l | Triglyceride Supertrate, Cholesterol HDL Supertrate Cholesterol (all available through Bayer) |
| Sodium Fluoride | 0.05 g/l | 0.0–0.50 g/l | Other halides |
| Sulfasalazine | 0.10 g/l | 0.0–0.50 g/l | Other antioxidants |
| α-Tocopherol (Vitamin E) | 0.05 g/l | 0.0–0.30 g/l | Ascorbic acid, BHT, Deferoximine Mesylate, Probucol, Rutin |

TABLE 6

| Cell | Range (approximate % of white blood cells) |
|---|---|
| Lymphocytes | 20 to 45% |
| Monocytes | 2 to 10% |
| Neutrophils | 40 to 75% |
| Eosinophil | 1 to 6% |
| Basophils | Up to 1% |

Further Alternative Exemplary Embodiment

For the red blood cell component, a diluent containing Mg Gluconate and EDTA (e.g., about 3.92 g/l Mg Gluconate; 7.04 g/l EDTA-Disodium; 2.68 gl $NA_2HPO_4$; glucose 6 g/l; and antimicrobials (pH of 7.1 and osmolarity using KCl of about 300)) stabilizes red cells so that red cell parameters are stable for 200 days.

The white blood cell component is prepared from fresh human white blood cells. The cells are washed free of red blood cells and platelets using the above diluent. The cells are suspended in phosphate buffered saline with an osmolarity of 280 and pH of 7.2. A solution of 20% Nuosept 145 (Huls America) is mixed with the white blood cells 1:1 to give a final concentration of about 10% (e.g., 9.11%). The mixture is placed at a temperature of about 37° C. to about 50° C. for six days or more. Thereafter, the cells are washed one or more times (e.g., 3 times) in a suitable diluent, e.g., a diluent such as Table 1, centrifuged (e.g., about 900 rpm for 10 minutes) and resuspended in a diluent such as in Table 1 (having no glucose and a pH of about 7).

The platelet component is prepared by washing human platelets free from whole blood components by low speed centrifugation (900 RPM for 10 min.). The platelets are then stabilized by addition of a low level of glutaraldehyde. The platelets are stabilized by mixing 1:1 with the magnesium gluconate diluent containing 0.075% glutaraldehyde (final concentration of 0.037% glutaraldehyde). After a 22° C. incubation, the cells are again washed in the diluent and are ready for use. The same procedure can be used for bovine or porcine.

The reticulocytes are prepared by encapsulation of yeast-RNA as described in U.S. Pat. No. 5,432,089, incorporated by reference.

The white blood cell component may be set up with red blood cells for achieving differential stability, such as by maintaining them at about 22° C. for about 20 days.

The final control contains the following cellular concentrations (Table 7), exhibits a histogram/scattergram profile that includes a properly positioned five-part differential of white blood cells and reticulocytes, substantially approximating whole blood and is stable for 200 days or more. This control provides such results for the Cell Dyn series, the Bayer H-3, and the Sysmex SF instruments.

TABLE 7

| Values | WBC | % N | % L | % M | % E | % B | RBC | RBCo | HCT | MCV | MCHC | RDW | % R | IRF | PLTo | PLTi | MPV |
|---|---|---|---|---|---|---|---|---|---|---|---|---|---|---|---|---|---|
| Low | 3.65 | 43.1 | 41.7 | 11.0 | 1.94 | 2.32 | 3.82 | 3.80 | 30.8 | 80.6 | 34.9 | 13.1 | 5.38 | .212 | 67.6 | 69.4 | 10.2 |
| Normal | 7.92 | 55.9 | 31.0 | 10.4 | 1.31 | 1.50 | 5.01 | 4.97 | 42.8 | 85.5 | 35.0 | 13.0 | 2.79 | .184 | 179.0 | 196.0 | 9.90 |
| High | 19.2 | 59.9 | 23.3 | 14.8 | 1.86 | .213 | 5.51 | 5.39 | 48.6 | 88.2 | 33.8 | 16.4 | .736 | .190 | 381.0 | 443.0 | 10.2 |

Accordingly, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims. All patents and other publications cited herein are expressly incorporated by reference.

We claim:

1. A method of assuring quality of a hematology instrument, comprising the steps of:
    a) providing a multi-parameter automated hematology instrument;
    b) providing in a known reference quantity:
        a. a first component for simulating human reticulocytes for detection by said multiparameter hematology analysis instrument;
        b. a second component for simulating human nucleated red blood cells for detection by said multiparameter hematology analysis instrument;
        c. a white blood cell component that is prepared from white blood cell analogs and is capable of exhibiting a five-part differential, upon detection by said multiparameter hematology analysis instrument;
    c) counting the population number per component type, of an admixture from said step (b), with said multi-parameter automated hematology instrument; and
    d) comparing the population number per component type obtained from step c) above with said known reference quantity for each component type.

2. The method of claim 1, wherein said analogs are provided from human white blood cells.

3. The method of claim 1, wherein said analogs are provided from red blood cells.

4. The method of claim 1, wherein said second component is prepared from avian red blood cells.

5. The method of claim 4 wherein said avian red blood cells are chicken red blood cells.

6. The method of claim 1, wherein said white blood cell component has been contacted with an aldehyde.

7. The method of claim 4 wherein said avian red blood cells are turkey red blood cells.

8. The method of claim 6 wherein said aldehyde is formaldehyde.

9. The method of claim 6 wherein said aldehyde is glutaraldehyde.

10. The method of claim 1, wherein said white blood cell component has been contacted with a heterocyclic urea.

11. The method of claim 1, wherein said second component further comprises a component for simulating human red blood cells for detection by said multiparameter hematology analysis instrument.

12. The method of claim 11, wherein said component for simulating red blood cells comprises human red blood cells.

13. The method of claim 11, wherein said second component further comprises a component for simulating human platelets for detection by said multiparameter hematology analysis instrument.

14. The method of claim 13, wherein said platelet component comprises simulated platelets.

15. The method of claim 14, wherein said simulated platelets comprise stabilized human platelets or platelets simulated from goat, bovine or porcine cells.

16. The control composition of claim 1, wherein said first component comprises goat red blood cells.

17. The method of claim 1 wherein said white blood cell component has been fixed by heat.

18. The method of claim 1 wherein said white blood cell component has been fixed by at least one chemical agent.

19. The method of claim 18 wherein said chemical agent is from the group consisting of alcohol and urea.

20. The method of claim 1 wherein said white blood cell component has been fixed by a combination of heat and at least one chemical agent.

21. A method of assuring quality of a hematology instrument, comprising the steps of:
   a) providing a multi-parameter automated hematology instrument;
   b) providing in a known reference quantity:
      a. a component for simulating human reticulocytes for detection by said multiparameter hematology analysis instrument; and
      b. a white blood cell component prepared from white blood cell analogs, said white blood cell component being suspended in ad isotonic suspension including a lipoprotein, and being capable of exhibiting a five-part differential, upon detection by said multiparameter hematology analysis instrument, said white blood cell component further including a component for simulating human nucleated red blood cells for detection by said multiparameter hematology analysis instrument;
   c) counting the population number per component type with said multi-parameter automated hematology instrument; and
   d) comparing the population number per component type obtained from step c) above with said known reference quantity for each component type.

22. The method of claim 21, wherein said component for simulating human reticulocytes is prepared from blood of an anemic animal.

23. The method of claim 21, wherein said component for simulating human reticulocytes is prepared from blood of an anemic pig.

24. The method of claim 21, wherein said component for simulating human reticulocytes is prepared from blood of an anemic goat.

25. The method of claim 21, wherein said component for simulating human reticulocytes is prepared from blood of an anemic rabbit.

26. The method of claim 21, wherein said white blood cell component further comprises stabilized red blood cells.

27. The method of claim 26 wherein said stabilized red blood cells are prepared in a substantially glucose free environment.

28. The method of claim 26 wherein said stabilized red blood cells are contained in a diluent including phosphate buffered saline with PEG.

29. The method of claim 28 wherein said diluent includes an EDTA preservative.

30. The method of claim 29 wherein said diluent includes magnesium gluconate.

31. The method of claim 30 wherein said diluent includes an antioxidant.

32. The method of claim 31 wherein said diluent includes about 2% bovine serum albumen.

33. The method of claim 21, wherein said white blood cell analogs are prepared from red blood cells.

34. A method of assuring quality of a hematology instrument, comprising the steps of:
   a) providing a multi-parameter automated hematology instrument;
   b) providing in a known reference quantity:
      a. a component for simulating human reticulocytes for detection by said multiparameter hematology analysis instrument;
      b. a component for simulating human nucleated red blood cells for detection by said multiparameter hematology analysis instrument;
      c. a component for simulating human red blood cells for detection by said multiparameter hematology analysis instrument;
      d. a component for simulating human platelets for detection by said multiparameter hematology analysis instrument, and
      e. a white blood cell component that is prepared from white blood cell analogs, said white blood cell component being suspended in an isotonic suspension including a lipoprotein, and being capable of exhibiting a five-part differential, upon detection by said multiparameter hematology analysis instrument;
   c) counting the population number per component type with said multi-parameter automated hematology instrument; and
   d) comparing the population number per component type obtained from step c) above with said known reference quantity for each component type.

35. The method of claim 34 wherein said white blood cell components are prepared from human cells.

36. The method of claim 34 wherein said white blood cell components are prepared from red blood cells.

37. The method of claim 34 wherein said reticulocyte component is prepared by encapsulation of red blood cells.

38. The method of claim 34 wherein said red blood cells are prepared in a substantially glucose free environment.

39. The method of claim 34 wherein said components are prepared in a manner to preserve surface antigens.

40. A method of assuring quality of a hematology instrument, comprising the steps of:

a) providing a multi-parameter automated hematology instrument;
b) providing in a known reference quantity:
   a. a component for simulating human reticulocytes;
   b. a component for simulating human nucleated red blood cells for detection by said multiparameter hematology analysis instrument;
   c. a component for simulating human red blood cells for detection by said multiparameter hematology instrument;
   d. a reticulated platelet component; and
   e. a white blood cell component that is prepared from white blood cell analogs that are fixed by at least one chemical, said white blood cell component being suspended in an isotonic suspension including a lipoprotein, and being capable of exhibiting a five-part differential, upon detection by said multiparameter hematology analysis instrument;
c) counting the population number per component type with said multi-parameter automated hematology instrument;
d) outputting the results of said counting; and
e) comparing the population number per component type obtained from step c) above with said known reference quantity for each component type.

41. The method of claim 40 wherein said component for simulating reticulocytes is prepared by encapsulation of red blood cells.

42. The method of claim 40 wherein said component for simulating reticulocytes is prepared from the blood of an anemic animal.

43. The method of claim 40 wherein said reference quantity further includes platelets for detection by said multiparameter hematology instrument.

44. The method of claim 40 wherein said white blood cell analog is further fixed by heating.

45. The method of claim 40 wherein said white blood cell component is prepared from red blood cells.

46. The method of claim 40 wherein said red blood cells are prepared in a substantially glucose free environment.

47. The method of claim 40 wherein said components are processed in a manner to preserve surface antigens.

48. The method of claim 40 wherein said white blood cell component includes at least three subcomponents selected from the group consisting of lymphocytes, monocytes, neutrophils, basophils and eosinophils.

49. The method of claim 40 wherein said white blood cell component is prepared from human white blood cells.

50. A method of assuring quality of a hematology instrument, comprising the steps of:
a) providing a multi-parameter automated hematology instrument;
b) providing in a known reference quantity:
   a. a component for simulating human reticulocytes for detection by said multiparameter hematology analysis instrument;
   b. a component for simulating human nucleated red blood cells for detection by said multiparameter hematology analysis instrument;
   c. a component for simulating human red blood cells for detection by said multiparameter hematology instrument;
   d. a component for simulating human platelets for detection by said multiparameter hematology instrument;
   e. a component for simulating human reticulated platelets for detection by said multiparameter hematology instrument; and
   f. a white blood cell component that is prepared from white blood cell analogs that are fixed by at least one chemical, said white blood cell component being suspended in an isotonic suspension including a lipoprotein, and being capable of exhibiting a five-part differential, upon detection by said multiparameter hematology analysis instrument;
c) counting the population number per component type with said multi-parameter automated hematology instrument;
d) outputting the results of said counting; and
e) comparing the population number per component type obtained from step c) above with said known reference quantity for each component type.

51. The method of claim 50 wherein said components are processed in a manner to preserve surface antigens.

52. The method of claim 50 wherein said white blood cell component is prepared from human white blood cells.

53. The method of claim 50 wherein said white blood cell component is prepared from red blood cells.

* * * * *

UNITED STATES PATENT AND TRADEMARK OFFICE
CERTIFICATE OF CORRECTION

PATENT NO. : 6,403,377 B1
DATED : June 11, 2002
INVENTOR(S) : Wayne L. Ryan et al.

It is certified that error appears in the above-identified patent and that said Letters Patent is hereby corrected as shown below:

Column 17,
Line 51, replace "ad" with -- an --.

Signed and Sealed this

Eighteenth Day of February, 2003

JAMES E. ROGAN
*Director of the United States Patent and Trademark Office*